US012098406B2

(12) United States Patent
Chandler et al.

(10) Patent No.: US 12,098,406 B2
(45) Date of Patent: *Sep. 24, 2024

(54) FORMULATIONS FOR DRYING BACTERIAL CELL EXTRACTS

(71) Applicant: Sutro Biopharma, Inc., South San Francisco, CA (US)

(72) Inventors: Martin Chandler, South San Francisco, CA (US); Kirk Hayenga, South San Francisco, CA (US); Henry Heinsohn, South San Francisco, CA (US)

(73) Assignee: Sutro Biopharma, Inc., South San Francisco, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 17/852,951

(22) Filed: Jun. 29, 2022

(65) Prior Publication Data

US 2023/0167475 A1 Jun. 1, 2023

Related U.S. Application Data

(63) Continuation of application No. 16/841,307, filed on Apr. 6, 2020, now Pat. No. 11,408,021, which is a continuation of application No. 15/542,396, filed as application No. PCT/US2016/012599 on Jan. 8, 2016, now Pat. No. 10,648,010.

(60) Provisional application No. 62/101,266, filed on Jan. 8, 2015.

(51) Int. Cl.
*C12P 21/00* (2006.01)
*C07K 14/535* (2006.01)
*C07K 16/00* (2006.01)
*C12P 1/04* (2006.01)
*C12P 21/02* (2006.01)

(52) U.S. Cl.
CPC ............ *C12P 21/00* (2013.01); *C07K 14/535* (2013.01); *C07K 16/00* (2013.01); *C12P 1/04* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 6,905,843 B1 | 6/2005 | Endo et al. | |
| 7,048,915 B2 | 5/2006 | Kuroita et al. | |
| 10,648,010 B2 | 5/2020 | Chandler et al. | |
| 2002/0039771 A1 | 4/2002 | Peters et al. | |
| 2003/0199076 A1 | 10/2003 | Kuroita et al. | |
| 2012/0230976 A1 | 9/2012 | Helmerhorst et al. | |
| 2018/0002732 A1 | 1/2018 | Chandler et al. | |

FOREIGN PATENT DOCUMENTS

| | | |
|---|---|---|
| EP | 259739 | 3/1988 |
| EP | 0259739 E1 | 3/1988 |
| WO | 2014004639 A1 | 1/2014 |
| WO | 2016112258 A1 | 7/2016 |

OTHER PUBLICATIONS

Basholli-Salihu et al., "Effect of Lyoprotectants on β-glucosidase Activity and Viability of Bifidobacterium Infantis After Freeze-Drying and Storage in Milk and Low pH Juices", LWT-Food Science and Technology, vol. 57, 2014, pp. 276-282.
Calhoun et al., "Chapter 1:Energy Systems for ATP Regeneration in Cell-Free Protein Synthesis Reactions", In Vitro Transcription and Translation Protocols, Second Edition, Methods in Molecular Biology, vol. 375, 2007, pp. 3-17.
Devaldez et al., "Effect of Drying Medium on Residual Moisture Content and Viability of 5, 14, 15 Freeze-Dried Lactic Acid Bacteria", Applied And Environmental Microbiology, vol. 49, No. 2,, Feb. 1985, pp. 413-415.
EP16735454.7 , "Extended European Search Report", Jun. 26, 2018, 11 pages.
Leach et al., "The Death of Micro-Organisms During Drying in Relation to Solute Concentration and Drying Temperature", Journal of General Microbiology, vol. 21, 1959, pp. 658-665.
Nechvatal et al., "Fecal Collection, Ambient Preservation, and DNA Extraction for PCR Amplification of Bacterial and Human Markers from Human Feces", Journal of Microbiological Methods, vol. 72, No. 2, 2008, pp. 124-132.
PCT/US2016/012599 , "International Preliminary Report on Patentability", Jul. 20, 2017, 10 pages.
PCT/US2016/012599 , "International Search Report and Written Opinion", Mar. 11, 2016, 11 pages.
Smith et al., "Lyophilized *Escherichia coli*-Based Cell-Free Systems for Robust, High-Density, Long-Term Storage", Biotechniques, vol. 56, No. 4, Apr. 2014, pp. 186-193.
Teather , "Maintenance of Laboratory Strains of Obligately Anaerobic Rumen Bacteria", Applied And Environmental Microbiology, vol. 44, No. 2, Aug. 1982, pp. 499-501.
Valdez et al., "Effect of Drying Medium on Residual Moisture Content and Viability of Freeze-Dried Lactic Acid Bacteria", Applied and Environmental Microbiology, vol. 49, No. 2, Feb. 1985, pp. 413-415.
Zhao et al., "Effect of Protective Agents, Freezing Temperature, Rehydration Media on Viability of Malolactic Bacteria Subjected to Freeze-Drying", Journal of Applied Microbiology, vol. 99, No. 2, 2005, pp. 333-338.

*Primary Examiner* — Robert J Yamasaki
(74) *Attorney, Agent, or Firm* — Kilpatrick Townsend and Stockton LLP

(57) ABSTRACT

This invention provides for an improved method of stabilizing freeze dried bacterial extracts with a carbohydrate lyoprotectant such that the extracts can be for use in cell free protein synthesis. Also provided herein are formulations for stable, freeze dried bacterial extracts that when stored at room temperature retain at least about 70% protein synthesis activity compared to undried frozen bacterial extracts.

28 Claims, No Drawings

FORMULATIONS FOR DRYING BACTERIAL CELL EXTRACTS

CROSS-REFERENCES TO RELATED APPLICATIONS

This application is a Continuation of U.S. application Ser. No. 16/841,307, filed Apr. 6, 2020, which is a Continuation of U.S. application Ser. No. 15/542,396, filed Jul. 7, 2017, which is the U.S. National Stage Entry under § 371 of International Application No. PCT/US2016/012599, filed Jan. 8, 2016, which claims the benefit of priority to U.S. Provisional Application No. 62/101,266, filed Jan. 8, 2015, the disclosures of which are hereby incorporated by reference in their entireties for all purposes.

FIELD OF THE INVENTION

This invention relates to formulations and methods for freeze drying bacterial cell extracts for use in cell free protein synthesis (CFPS). The specific carbohydrate lyoprotectant(s) described herein advantageously provide increased stability during long-term storage at 4° C. or higher.

BACKGROUND OF THE INVENTION

The use of bacterial extracts for generating proteins of interest in cell free protein synthesis reactions (CFPS) has been expanding from a laboratory scale to commercial scale. There is a continuing need to make the process more economical. A part of this need includes improved methods for storing and stabilizing bacterial extracts. Prior art methods included the use of various additives; freezing and thawing; spray-drying or conventional lyophilization. Drying bacterial extract has obvious advantages of reduced volume but typically resulted in significant reduction in the ability of the extracts to generate the proteins of interest.

In conventional freeze-drying (lyophilization) of bacterial extracts, vacuum pressure lowers the boiling temperature of water in the extract and enables the bacterial extracts to be dried at a lower temperature. The process reduces thermal degradation, relative to higher temperature drying procedures. Typically, a pressure gradient is created within the extract, driving mass transfer as vaporization occurs, and increasing heat transfer such that a heat gradient forms. Due to the heat gradient, outer portions of the sample tend to dry first, causing the surface layer to become more isolating for interior regions of the material and preventing more rapid heat transfer. Conventional lyophilization can lower the viability of biologically-active materials in bacterial extracts.

In situ vaporization provides an expansive force in the sample as water vapor escapes, maintaining a more porous structure with increased surface area for sublimation. Microwave radiation in a vacuum chamber (radiant energy vacuum) is used to remove water to dehydrate biological materials (e.g., proteins, enzymes, nucleic acids, macromolecules, etc.). In some cases, biological material is frozen at low temperature in a vacuum chamber and radiant energy applied, such that the ice in the material is sublimated. In other cases the biological material is frozen prior to entering the vacuum chamber. This microwave radiation sublimation process prevents damage to temperature-sensitive biological materials from elevated temperatures and increases the drying rate and decreases drying times, relative to conventional freeze-drying procedures.

Formulations of liquid extract prior to freeze drying enable integration of non-volatile additives into the dried extract. The presence of additive(s) has been shown to improve or increase the extract stability during storage. For example, an inositol can be added to wheat germ extracts for use in cell free protein synthesis (see, U.S. Pat. No. 7,048,915).

BRIEF SUMMARY OF THE INVENTION

In a first aspect, the present invention provides a method for stabilizing a freeze dried bacterial extract for cell free protein synthesis. The method includes the steps of: (i) combining a bacterial extract comprising lysed bacterial components, wherein the extract is able to synthesize a target protein from a template nucleic acid encoding the target protein in cell free protein synthesis, with a carbohydrate composition, wherein the carbohydrate composition constitutes about 20-100% (% of total carbohydrate composition) sucrose and 0-80% (% of total carbohydrate composition) of a non-sucrose portion comprising mannitol, sorbitol, dextran, or mixtures thereof to yield a mixture; and (ii) freeze drying the mixture to produce the stable, freeze dried bacterial extract having an about 0.6-2:1 (w/w) ratio of carbohydrate to bacterial components. In some embodiments, the method also includes (iii) rehydrating the freeze dried bacterial extract; and (iv) synthesizing the target protein under conditions that support a cell free protein synthesis reaction. In some instances, the step of freeze drying includes lyophilizing. The carbohydrate composition can constitute about 20-100% sucrose, e.g., about 20%, 25%, 30%, 35%, 40%, 45%, 50%, 55%, 60%, 65%, 70%, 75%, 80%, 85%, 90%, 95%, or 100% sucrose. The carbohydrate composition can constitute a non-sucrose portion that includes mannitol, sorbitol, dextran or mixtures thereof. The carbohydrate composition can constitute about 0-80% non-sucrose, e.g., about 20%, 25%, 30%, 35%, 40%, 45%, 50%, 55%, 60%, 65%, 70%, 75%, or 80% non-sucrose. The carbohydrate composition can constitute a non-sucrose portion that includes mannitol, sorbitol, dextran or mixtures thereof The stable, freeze dried bacterial extract can have an about 0.6-2:1 (w/w), about 0.6:1; 0.7:1, 0.8:1, 0.9:1, 1.0:1, 1.1:1, 1.2:1, 1.3:1, 1.4:1, 1.5:1, 1.6:1, 1.7:1, 1.8:1, 1.9:1 or 2.0:1 (w/w) ratio of carbohydrate to bacterial components.

The bacterial extract for use the present invention can be include template DNA (such as plasmid or linear DNA fragments), amino acids (including native or non-native amino acids), nucleotides, T7 RNA polymerase, an energy source (such as ATP, GTP and the like), and optionally, other factors that improve the synthesis, stability or activity of the selected protein of interest produced in the reaction. The bacterial extract can be an extract used in standard cell free protein synthesis (e.g., the Cytomim system).

The freeze dried bacterial extract can have an active oxidative phosphorylation system during cell free protein synthesis. In some embodiments, such a bacterial extract is from an Escherichia species. Non-limiting examples of Escherichia bacteria include *E. albertii, E. blattae, E. coli, E. fergusonii, E. hermannii, E. senegalensis,* and *E. vulneris.*

In some embodiments, the carbohydrate composition constitutes 100% sucrose. In other embodiments, the non-sucrose portion of the carbohydrate composition can include at least about 75% of the carbohydrate composition. In some instances, the non-sucrose portion is about 75% or more, e.g., about 75%, 76%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the carbohydrate composition.

In some embodiments, the freeze dried bacterial extract has less than or equal to about 2.6% (w/w) residual water. The extract can have about 2.6% (weight/weight; w/w) or less, e.g., about 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1% or 0% (w/w) residual water.

In some embodiments, the freeze dried bacterial extract when stored at about 20-22° C. (e.g., room temperature) for 25 days or more and then is rehydrated has about 70% or more protein synthesis activity, compared to that of a control bacterial extract. The extract can be stored at about room temperature or lower, e.g., 22° C., 21° C., 20° C., 10° C., 8° C., 7° C., 6° C., 5° C. 4° C., 0° C., −20° C., −78.5° C., −80° C., −120° C., −150° C., −195° C., −200° C., −225° C., −250° C., −273° C. and −273.15° C., rehydrated and used in a cell free protein synthesis reaction, wherein the rehydrated extract has about 70% or more, e.g., 70%, 71%, 72%, 73%, 74%, 75%, 76%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% protein synthesis activity compared to a control bacterial extract. In some embodiments, the control bacterial extract is a bacterial extract (e.g., lysed bacterial components able to synthesize a target protein from a template nucleic acid encoding the target protein during CFPS) that has not been freeze dried. In other embodiments, the control bacterial extract has not been freeze dried and contains none of the formulation additives described herein. The control bacterial extract can be stored at at least about −80° C., e.g., −80° C. or less.

The bacterial extract can have an active oxidative phosphorylation system during cell free protein synthesis. In some embodiments, the bacterial extract is from an Escherichia species. Non-limiting examples of Escherichia bacteria include *E. albertii*, *E. blattae*, *E. coli*, *E. fergusonii*, *E. hermannii*, *E. senegalensis*, and *E. vulneris*.

In a second aspect, the present invention provides a freeze dried bacterial extract for cell free protein synthesis having a water content of less than or equal to about 1.5% (w/w) residual water, e.g., 1.5%, 1.4%, 1.3%, 1.2%, 1.1%, 1.0%, 0.9%, 0.8%, 0.7%, 0.6%, 0.5%, 0.4%, 0.3%, 0.2%, 0.1% or 0% (w/w) residual water. The freeze dried bacterial extract includes dried, lysed bacterial components able to synthesize upon rehydration a target protein from a template nucleic acid encoding the target protein; and a carbohydrate composition in about 0.8-1.5:1.0 (w/w) ratio of carbohydrate to dried bacterial components, wherein the carbohydrate composition constitutes about 20-100% sucrose and a non-sucrose portion comprising mannitol, sorbitol, dextran or mixtures thereof. The carbohydrate composition can be in about 0.6-2.0: 1; e.g., about 0.6:1; 0.7:1, 0.8:1, 0.9:1, 1.0:1, 1.1:1, 1.2:1, 1.3:1, 1.4:1, 1.5:1, 1.6:1, 1.7:1, 1.8:1, 1.9:1 or 2.0:1 (w/w) ratio of carbohydrate to bacterial components. The carbohydrate composition can constitute about 20-100% sucrose, e.g., about 20%, 25%, 30%, 35%, 40%, 45%, 50%, 55%, 60%, 65%, 70%, 75%, 80%, 85%, 90%, 95%, or 100% sucrose. The carbohydrate composition can constitute a non-sucrose portion that includes mannitol, sorbitol, dextran or mixtures thereof. In some embodiments, the carbohydrate composition constitutes 100% sucrose.

In some embodiments, the non-sucrose portion is at least about 75%, e.g., about 75%, 76%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the total carbohydrate composition.

In some embodiments, the freeze dried bacterial extract has less than or equal to about 1.0% (w/w), e.g., about 1.0%, 0.9%, 0.8%, 0.7%, 0.6%, 0.5%, 0.4%, 0.3%, 0.2%, 0.1% or 0% (w/w) residual water.

The freeze dried bacterial extract, when stored at about 20-22° C. (e.g., room temperature) for 25 days or more, e.g., 25 days, 1 month, 50 days, 2 months, 3 months, 4 months, 5 months, 6 months, 7 months, 8 months, 9, months, 10 months, 11 months, 1 year or more, and then rehydrated, has about 70% or more protein synthesis activity compared to that of a control bacterial extract. The extract can be stored at about room temperature or lower, e.g., 22° C., 21° C., 20° C., 10° C., 4° C., 0° C., −20° C., −78.5° C., −80° C., −120° C., −195° C., and −320° C., rehydrated and used in a cell free protein synthesis reaction, wherein the rehydrated extract has about 70% or more, e.g., 70%, 71%, 72%, 73%, 74%, 75%, 76%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% protein synthesis activity compared to a control bacterial extract. The freeze dried bacterial extract can be stored for about 50 days or more, e.g., 50 days, 2 months, 3 months, 4 months, 5 months, 6 months, 7 months, 8 months, 9, months, 10 months, 11 months, 1 year or more. The freeze dried bacterial extract can be stored for about 150 days or more.

In some embodiments, the control bacterial extract is a bacterial extract that has not been freeze dried. In other embodiments, the control bacterial extract has not been freeze dried and contains none of the formulation additives (e.g., carbohydrate additives or lyoprotectants) described herein. The control bacterial extract can be stored at at least about −80° C., e.g., −80° C. or less.

In a third aspect, provided herein is a formulation of a freeze dried bacterial extract for cell free protein synthesis having a water content of less than or equal to about 1.5% (w/w) residual water. The extract includes dried, lysed bacterial components able to synthesize upon rehydration a target protein from a template nucleic acid encoding the target protein; and a carbohydrate composition in about 0.6-2.0:1.0 (w/w) ratio of carbohydrate to bacterial components, wherein the carbohydrate composition constitutes about 22% sucrose (% weight of total carbohydrate composition), 22% sorbitol, 46% mannitol, and 10% dextran.

In a fourth aspect, provided herein is another formulation of a freeze dried bacterial extract for cell free protein synthesis having a water content of less than or equal to about 1.5% (w/w) residual water. The extract includes dried, lysed bacterial components able to synthesize upon rehydration a target protein from a template nucleic acid encoding the target protein; and a carbohydrate composition in about 0.6-2.0:1.0 (w/w) ratio of carbohydrate to bacterial components, wherein the carbohydrate composition constitutes about 100% sucrose (% weight of total carbohydrate composition).

Carbohydrate based lyoprotectants have been used with preparations of individual, purified proteins, and not with complex cellular extracts. The inventors have surprisingly discovered that the protein synthesis activity of specific carbohydrate additive-containing freeze dried bacterial extracts is preserved, even when the extracts are stored at 4° C. or higher. As such, the invention described herein provides compositions of improved freeze dried bacterial extracts containing one or more carbohydrate lyoprotectant, as well as, methods for making thereof. These freeze dried bacterial extract compositions are useful for CFPS. As such, commerical protein synthesis reactions can be performed using freeze dried bacterial extracts instead of fresh or frozen bacterial extracts.

Other objects, features, and advantages of the present invention will be apparent to one of skill in the art from the following detailed description and figures.

DETAILED DESCRIPTION OF THE INVENTION

This invention provides compositions and methods for making freeze dried bacterial extracts for use in cell-free protein synthesis reactions. The invention is based, in part, on the discovery of a method for stabilizing a freeze dried bacterial extract having a 0.6-2:1 (w/w) ratio of carbohydrate to bacterial components and a water content of less than equal to 1.5% (w/w) residual water. The freeze dried bacterial extract formulation described herein produces an improved bacterial lysate that retains its capacity to produce biomolecules, e.g., proteins that are equal to or substantially equal to extracts that have not been freeze-dried.

Standard methods in molecular biology are described (Maniatis et al. (1982) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif.). Standard methods also appear in Bindereif, Schon, & Westhof (2005) Handbook of RNA Biochemistry, Wiley-VCH, Weinheim, Germany which describes detailed methods for RNA manipulation and analysis, and Walker, J.M., (2009) The Protein Protocols Handbook, 3r$^d$ ed., Humana Press, New York, N.Y. which describes detailed method for protein manipulation and analysis.

Definitions

As used herein, the following terms have the meanings ascribed to them unless specified otherwise.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a," "and," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The term "bacterial extract" refers to a bacterial cell lysate or a fraction thereof wherein the cellular extract is able to synthesis a protein from a nucleic acid template without adding other components. In other words, the bacterial extract contains an energy source, such as ATP, GTP and the like. A bacterial extract can be a portion of a lysate from which other cellular components of the lysate have been separated by centrifugation, filtration, selective precipitation, selective immunoprecipitation, chromatography, or other methods. It also includes lysates or fractions thereof that contain exogenous material such as preservatives, stabilizers and reagents that enhance cell free protein synthesis (CFPS). The term "bacterial extract" can refer to a preparation of an in vitro reaction mixture able to transcribe DNA into mRNA and/or translate mRNA into polypeptides. The mixture may include ribosomes, ATP, amino acids, and tRNAs. The mixture may be derived directly from lysed bacteria, from purified components or combinations of both.

The term "the extract is able to synthesize a target protein from a template nucleic acid encoding the target protein in cell free protein synthesis" refers a lysed bacterial extract containing all the necessary bacterial components needed to synthesize a protein of interest in a cell free protein without the addition of other components of a bacterial extract.

"Cell free protein synthesis" or "CFPS" refers to the in vitro synthesis of nucleic acids, polypeptides, small molecules and/or viral particles in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc.; and co-factors, enzymes and other reagents that are necessary for the synthesis, e.g. ribosomes, uncharged tRNAs, tRNAs charged with natural and/or unnatural amino acids, polymerases, transcriptional factors, tRNA synthetases, etc.

The term "freeze dried bacterial extract" refers to a bacterial extract that has been subjected to freeze drying, lyophilization, in situ vaporization, microwave radiation sublimation, and the like.

The term "stable, freeze dried bacterial extract" refers to a freeze dried bacterial extract that essentially retains its physical and chemical stability and integrity upon storage, e.g., long term storage of about 25 days or more.

The term "control bacterial extract" refers to a bacterial extract that is free of formulation additives, such as those described herein. In other words, a control bacterial extract can be an unformulated bacterial extract. The control extract can be freeze dried and/or stored at various temperatures, such as −80° C., −20° C., 4° C., 20° C., and 37° C.). The control extract can be an unformulated, freeze dried bacterial extract. The control bacterial extract can be an unformulated, frozen bacterial extract. Alternatively, the control bacterial extract has not been freeze dried. In some instances, the control bacterial extract is a fresh bacterial extract.

The term "lysed bacterial components" refers to cellular components of a lysed bacterium.

The term "carbohydrate" refers to a macromolecule consisting of carbon, hydrogen, and oxygen atoms and having an empirical formula $C_m(H2O)_n$, wherein m and n may be different numbers. Carbohydrates include monosaccharides, disaccharides, oligosaccharides, and polysaccharides.

The term "rehydrating" or "reconstituting", in the context of a freeze dried bacterial extract, refers to suspending a freeze dried bacterial extract in a diluent such as water to disperse the components of the bacterial extract.

The term "water content" refers to the quantity of water contained in a material.

The term "residual water" or "residual moisture" refers to the quantity of water contained in a material after the material has been processed, such as freeze dried.

The term "protein synthesis activity" refers to the protein yield (e.g., the amount of protein) from a protein synthesis reaction to produce a target protein relative to a control protein synthesis reaction.

The term "freeze drying" refers to a process of reducing the water content of a material that includes subjecting the material to freezing. Freeze drying such as lyophilization can include the steps of freezing the material and sublimating the material by reducing the surrounding pressure.

The term "lysate" is any cell derived preparation comprising the components required for protein synthesis machinery, wherein such cellular components are capable of expressing a nucleic acid encoding a desired protein where a majority of the biological components are present in concentrations resulting from the lysis of the cells rather than having been reconstituted. A lysate may be further altered such that the lysate is supplemented with additional cellular components, e.g. amino acids, nucleic acids, enzymes, etc. The lysate may also be altered such that additional cellular components are removed or degraded following lysis.

The terms "polypeptide," "peptide" or "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "active oxidative phosphorylation system" in the context of a bacterial extract, refers to a bacterial extract that exhibits active oxidative phosphorylation during protein synthesis. For example, the bacterial extract can generate ATP using ATP synthase enzymes and reduction of oxygen. It will be understood that other translation systems known in the art can also use an active oxidative phosphorylation during protein synthesis. The activation of oxidative phosphorylation can be demonstrated by inhibition of the pathway using specific inhibitors, such as electron transport chain inhibitors.

II. Detailed Description of Embodiments

A. Culturing Bacteria

Bacterial culturing is well known to those skilled in the art. A bacterial lysate derived from any strain of bacteria can be used in the methods of the invention. Bacteria suitable for use in cell free synthesis systems include gram-negative bacteria and gram-positive bacteria, for example, Enterobacteriaceae such as Escherichia, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, and Pseudomonas such as *P. aeruginsa*, and *Steptomyces*. In preferred embodiments, the bacteria used in the formulations and methods provided herein are from an Escherichia species, such as Escherichia coli or a derivative thereof.

The bacterial strain used to make the cell extract may have reduced nuclease and/or phosphatase activity which increases cell free synthesis efficiency. For example, the bacterial strain used to make the cell free extract can have mutations in the genes encoding the nucleases RNase E and RNase A. The strain may also have mutations to stabilize components of the cell synthesis reaction such as deletions in genes such as tnaA, speA, sdaA or gshA, which prevent degradation of the amino acids tryptophan, arginine, serine and cysteine, respectively, in a cell-free synthesis reaction. Additionally, the strain may have mutations to stabilize the protein products of cell-free synthesis such as knockouts in the proteases ompT or lonP.

The bacterial culture can be obtained as follows. The bacteria of choice are grown up overnight in any of a number of growth media and under growth conditions that are well known in the art and easily optimized by a practitioner for growth of the particular bacteria. In general, isolated strains of bacteria are grown in media until they reach balanced exponential growth phase or stationary phase. This can be between $10^6$ to $10^9$ cells per ml. In some embodiments, the culture is harvested when the pH of the culture rises above a set point indicating the depletion of glucose in the media. The bacterial culture can be grown to an $OD_{595-600}$ of 10 to 60, depending on the bacterial strain used. In some embodiments, the bacteria is cultured at a growth rate of about 0.06 to about 0.6 to about 0.8 doublings per hour.

The bacterial cells can be grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients. Optimal media and growth conditions are known for specific species. For example, *E. coli* are commonly grown in YT broth (yeast extract and tryptone) or variants thereof. The media can be defined (synthetic) or complex (undefined).

Bacterial cells can be transfected or transformed with expression or cloning vectors and cultured in conventional nutrient media modified as appropriate for inducing promoters, selecting transformations and preparing bacterial extracts, as described herein.

In some instances, the bacteria is cultured in aerobic conditions to induce protein expression, and then the culture is switched to anaerobic conditions, for example by bubbling nitrogen, argon, etc. through the culture medium.

When large amounts of bacteria are needed, continuous culturing means are employed instead of batch systems which are closed. These continuous systems involve the continued introduction of nutrients and removal of waste. Optimally, this permits the cells to be grown at a constant biomass concentration for extended periods. Two well-known systems are chemostats and turbidostats. In the chemostat system sterile media is fed in at a constant rate while media containing bacteria is removed at the same rate. The turbidostat system uses a photocell to measure absorbance or turbidity and regulates the inflow of sterile media and outflow of bacteria according to preset signals.

Methods of culturing bacteria are described in, e.g., Zawada et al., Biotechnol. Bioeng., 108(7):1570-1578 (2011); Zawada, J. "Preparation and Testing of E.coli S30 In Vitro Transcription Translation Extracts", Douthwaite, J.A. and Jackson, R.H. (eds.), Ribosome Display and Related Technologies: Methods and Protocols, Methods in Molecular Biology, vol. 805, pp. 31-41 (Humana Press, 2012); Jewett et al., Molecular Systems Biology: 4, 1-10 (2008); Shin J. and Norieaux V., I Biol. Eng., 4:8 (2010).

In some instances, an engineered *E. coli* strain (e.g., engineered K-12 derived E. coli strain KGK10) is cultured to mid-log phase ($OD_{595}$ of about 45 OD or about 140 g/L of cell wet weight) using glucose and amino acid fed-batch fermentation at a maximal growth rate of about 0.7 $h^{-1}$.

Glucose can be increased during culturing such that there is excess glucose during harvest. See, e.g., Zawada et al., Biotechnol. Bioeng., 108(7): 1570-1578 (2011).

B. Preparing Bacterial Extracts

Once the bacterial culture is ready for harvest, it can be cooled to 2-8° C., usually on ice or through heat exchangers when the culture is of a large scale. The culture can be centrifuged to separate the spent media from the cell paste (cell slurry). Preferred centrifuges include disk stack centrifuges, tubular bowl centrifuges, and other centrifuges for large or small scale bacterial cultures. The cell paste is typically resuspended in S30 buffer, any equivalent buffer solution, or water. S30 buffer comprises 10 mM Tris acetate, 14 mM magnesium acetate and 60 mM potassium acetate. In some embodiments, a 1:1, 2:1, 3:1, 4:1, 5:1, 6:1, 7:1, 8:1 or more dilution (liquid: solid; ml of buffer: gram weight of cells) is made for washing. The cell paste can be washed again in S30 buffer or any equivalent buffer, and centrifuged to remove any residual buffer. For small scale cultures, a second wash step is typically performed. At washing the cell paste (cell pellet) can be stored at −80° C. for use later or further processed by homogenization to lyse the cells.

A cell extract can be prepared from cultured bacteria, as described above. Cells that have been fermented overnight can be lysed by suspending the cell pellet in a suitable cell suspension buffer, and disrupting the suspended cells by sonication, breaking the suspended cells in a French press or with glass beads, continuous flow high pressure homogenization, or any other method known in the art useful for efficient cell lysis. The cell lysate is then centrifuged or filtered to remove large cell debris, including DNA, and cells that have not been lysed.

In some embodiments, the bacterial culture is pelleted by centrifugation at greater than 14,000 ×g for about 45 min at about 8-20° C. twice in a tubular bowl centrifuge in continuous or batch mode or a disc stack continuous centrifuge with a maximum bowl speed of about 12,000 rpm and a feed flow rate of about 3.0-3.3 L/min. The pelleted cells are resuspended and repelleted with S30 buffer. In some embodiments, the cells are stored at −80° C. for use later or processed by homogenization.

Prior to homogenization, the cell pellet can be resuspended in S30 buffer or an equivalent to produce a cell suspension. In some embodiments, a 1:1, 2:1, 3:1, 4:1, 5:1, 6:1, 7:1, 8:1 or more dilution (liquid: solid; ml of buffer: gram weight of cells) is created. Preferably, a 2:1 dilution is made such that 2 ml of S30 buffer is used per gram weight of cell pellet.

The cell suspension can be homogenized or disrupted in a standard high pressure homogenizer (e.g., an Avestin Emulsiflex C-55a Homogenizer) and/or microfluidizer (e.g., Microfluidics Microfluidizer) set at the appropriate pressure, such as 3,000 psi to produce a lysate. The homogenization step lyses the bacteria to release the necessary components required for protein synthesis, and in some aspects, formed inverted membrane vesicles provide energy for protein synthesis via respiration.

In some embodiments, the homogenizer pressure is at about 3,000-20,000 psi. In some embodiments, the homogenizer pressure is set at about 20,000 psi. In some embodiments, the speed (frequency setting) of the homogenizer is at about 20 Hz to about 60 Hz to produce flow rates of about 340 ml/min-1.0 L/min. Generally, flow rate is proportional to the frequency setting and can be varied independently from the homogenizing pressure. Preferably, the minimum speed setting for homogenizing steps is about 20 Hz with a flow rate of about 340 mL/min.

Bacterial lysates are also commercially available from manufacturers such Promega Corp., Madison, WI; Agilent Technologies, Santa Clara, CA; GE Healthcare Biosciences, Pittsburgh, PA; Life Technologies, Carlsbad, CA; and Roche Diagnostics, Basel, Switzerland.

Next, the lysate can be clarified by centrifugation such that from at least about 45% to about 85% or more, e.g., about 45%, 50%, 55%, 60%, 65%, 70%, 75%, 80%, 85% of the cell solids are separated from the cell free extract which is collected. In some embodiments, at least about 70%, 75%, 80%, 85%, 90%, or 95% of the cellular solids are separated by centrifugation. In some embodiments, the centrifugation is by a continuous centrifuge, e.g., disk stack centrifuge, tubular bowl centrifuge or appropriate centrifuge. In some embodiments, 200 L fermentation yields greater than 1.1 L clarified extract/kg of cell wet weight with a total protein concentration of about 20-25 g/L.

The extract can be filtered through one or more sterilizing grade filter membranes, e.g., a 0.45 µm filter membrane and/or a 0.22 µm filter membrane. A 0.45 µm filter membrane can be used first, and then a 0.22 µm filter membrane afterwards.

In some embodiments, the filtered extract is activated or pre-incubated at 30° C. for about 2-5 hours, preferably for about 2.5 hours. After pre-incubation, particulates from the extract can be separated by centrifugation, e.g., spinning at least 14,000 ×g for about 35 minutes.

The lysed bacterial extract can be aliquoted and frozen in liquid nitrogen before storing at −80° C. Optionally, a cell free synthesis reaction mix, as described herein, can be added to the cell free extract prior to freezing.

Methods of preparing a lysed bacterial extract are described in, e.g., Zawada, J. "Preparation and Testing of *E. coli* S30 In Vitro Transcription Translation Extracts", Douthwaite, J.A. and Jackson, R.H. (eds.), Ribosome Display and Related Technologies: Methods and Protocols, Methods in Molecular Biology, vol. 805, pp. 31-41 (Humana Press, 2012); Jewett et al., Molecular Systems Biology, 4, 1-10 (2008); Shin J. and Norieaux V., J. Biol. Eng., 4:8 (2010).

C. Carbohydrate Additives for Pre-Lyophilized Bacterial Extracts

The present invention is based, in part, on the unexpected discovery that specific carbohydrate additive(s) or lyoprotectant(s) (i.e., a stabilizer used to prevent denaturation of proteins during freeze drying and/or long term storage) when added to bacterial extracts prior to freeze-drying maintain their protein synthesis activity of the extracts in cell free protein synthesis. In fact, the particular formulations of the stable, freeze dried bacterial extracts described herein can be stored for at least 175 days at room temperature or at 4° C. and have at least 70% protein synthesis activity compared to a frozen extract containing no lyoprotectants or carbohydrate additives. Experiments described in Example 7 (see below) show that formulations with sucrose or a combination of sucrose and mannose have long-term storage stability, yet formulations with trehalose did not show activity. Surprisingly, dried extract formulations with raffinose, which has a higher glass transition temperature than sucrose, did not show better stability than dried extract formulations with sucrose.

In some embodiments, the additives include sucrose, and optionally, a non-sucrose compound, such as but not limited to, mannitol, sorbitol, dextran, and combinations thereof For instance, the composition of the additive can be 100% sucrose (% of the additive in the total additive mixture). Alternatively, the composition of additives can include 90% (% of the additive in the total additive mixture) sucrose and 10% mannitol. In other instances, the composition of the additives includes 22% sucrose, 22% sorbitol, 46% mannitol and 10% dextran. The composition can be about 20%-100% sucrose, about 0%-25% sorbital, about 0%-55% mannitol, and about 0%-15% dextran.

The additives can be mixed with a liquid lysed bacterial extract by combining a concentrated stock solution of one or more of the additives to achieve the preferred formulation of the freeze dried extract. For example, the liquid extract containing the additive(s) can have about 20 g/L-150 g/L, e.g., 20 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L, 100 g/L, 105 g/L, 110 g/L, 115 g/L, 120 g/L, 125 g/L, 130 g/L, 135 g/L, 140 g/L, 145 g/L, or 150 g/L of total dry weight of the additives per volume of lysed bacterial extract.

D. Other Additives

Other compounds, chemical, molecules, reagents, and the like can be added the lysed bacterial extract prior to freeze drying. In some cases, a buffer such as, but not limited to, a sodium chloride solution, a phosphate buffer or a citrate buffer can be mixed together (combined) with the lysed bacteria extract. In other cases, other lyoprotectants can be combined with the lysed extract. Non-limiting examples of additional lyoprotectants include, trehalose, lactose, maltose, ribose, mannose, fructose, sorbose, galactose, xylose, glucose, amylose, amylopectin, raffinose, glycogen, cellulose, bovine serum albumin, Ficoll 70, polyvinylpyrrolidone, propylene glycol, polyethylene glycol, pluronics, cyclodextrin, dextrin, inulin, skimmed milk powder, sodium ascorbate, hydroxypropyl-$\beta$-cyclodextrin, gelatin, glycerin, erythritol, glycerol, arabitol, xylitol, sorbital, inositol, monosodium glutamate, glycine, histidine, L-arginine, methionine, a methylamine (e.g., betaine), magnesium sulfate, dimethyl-succinate buffer, and combinations thereof.

E. Freeze Drying Bacterial Extracts

The additive containing bacterial extracts can be freeze dried (lyophilized) using standard methods as described in, for example, Smith et al., BioTechniques, 2014, 56(4):186-193. Briefly, the bacteria extract is loaded in to vials for shell freezing in a -40° C. ethanol bath and incubated for at least about 5 minutes. The vials are transferred to a freeze dryer and subjected one or more periods of freeze drying at the appropriate condition, such as at −60° C. and at high vacuum pressure, e.g., greater than 120 mTorr (<120 mTorr), with an ambient temperature of 19° C.-20° C. The freeze drying process is continued until at least about 98.5% of the estimated water content of the extract is removed.

Lyophilization can involve exposure of the frozen bacterial extracts to microwave radiation under partial vacuum. This process of dehydration surprisingly retains increased extract activity compared to aqueous extracts treated with conventional drying methods such as air-drying, spray-drying or standard lyophilization techniques.

Methods for freeze drying bacterial extracts with radiant energy provided in the form of microwave radiation under reduced pressure can also be used. This method has been practiced for many years, particularly in the food products industry. Recent studies in microwave vacuum dehydration show them to be rapid and energy-efficient procedures, which also minimize changes in product quality and degradation (Drouzas, A.E. and Schubert, H., I Food Engineering, 1996, 28(2):203-209).

Microwave radiation allows for adjustment of the rate of water removal, control of final water content, and maintenance of reduced temperatures during dehydration. The method also makes it possible to lower the microwave field strength as the material dries to avoid potential overheating. For microwave freeze drying with an overall duration of just a few hours, the exposure of the product to temperatures above 20° C. is far shorter so that most of its thermally sensitive components can be maintained. Drying of heat-labile compounds and preservation of biological components sensitive to residual moisture content in bacterial extracts is facilitated. Hence, microwave vacuum drying of frozen materials combines the advantages of vacuum or freeze drying and the rapidity of microwave drying.

As described in the Examples, samples are inserted into a stainless steel chamber or quartz vacuum chamber, where the vacuum pump provides reduced pressure. Means to monitor the sample are provided by a camera able to observe the samples within the vacuum chamber and data recorder in communication with the camera.

Exemplary detailed descriptions of radiant energy vacuum methods and apparatus that may be used in the invention can be found in U.S. Pat. No. 8,718,113, and U.S. App. Publication Nos. 2011/0209354, and 2010/0218395, the disclosures of which are incorporated by reference in their entirety for all purposes.

Alternatively, commercial microwave freeze drying apparatus are available through suppliers such as Püschner Microwave Power Systems (Schwanewede, Germany), Nanjing Sanle Microwave Technology Development co., Ltd. (Nanjing, China), INAP (MiVap, Marzling, Germany) and EnWave Corporation (Radiant Energy Vacuum (REV), Vancouver, B.C., Canada).

The method described herein can be used to freeze dry additive containing bacterial extract that is in a liquid state or a frozen state. Before performing such as a method, a frozen bacterial extract can be thawed at room temperature (e.g., 20° C.-22° C.) for about 30-40 minutes and/or aliquoted into appropriate volumes as determined by the drying method to be used.

For a liquid state, an aliquot typically about 0.25 ml to 2 ml of extract can transferred into a sterile glass vial and optionally, capped. The vial is loaded into a radiant energy vacuum machine or an equivalent thereof. Prior to applying vacuum vial cap is removed, if needed. The extract can be spun under vacuum at low speed to reduce liquid splashing and spillage. Preferably, the extract is spun under vacuum at about 200-1,000 rpm. The vacuum pressure can be less than 100 mTorr or range from 40-80 mTorr, preferably from 50-75 mTorr. When the temperature of the vial chamber reaches about 0-2° C., the microwave power is applied. Microwave power on average can be about 650 watts to about 2000 watts. Preferably, the liquid drying condition includes a total drying time of about 2,100 sec/0.5 ml of extract; microwave power at about 750 watts, spin speed of about 200 rpm, and a maximum temperature of about 35-38° C. Once the bacterial extract is dried, the vial can be capped, sealed with an aluminum cap, and stored at −80° C.

For a frozen state, an aliquot typically about 0.25 ml to 2 ml of extract can be transferred into a sterile glass vial, and optionally capped. The vial is loaded into a radiant energy vacuum machine or an equivalent thereof. Prior to applying vacuum, the vial cap is removed, if needed. The extracts can be spun under vacuum at about 200-1,000 rpm, preferably at about 500 rpm. The vacuum pressure can range from 40-80 mTorr, preferably 50-75 mTorr. When the temperature of the chamber reaches about −20° C. or when the extract is partially frozen, the microwave power is applied. Microwave power on average can be about 650 watts to about 1.3 kW. Preferably, the frozen drying condition includes a total drying time of about 3,000 sec/1.0 ml; microwave power at about 750 watts, spin speed of about 200 rpm, and a maximum temperature of about 35-38° C. The vial containing dried extract can be capped, sealed with an aluminum cap, and stored at −80° C.

In some embodiments, radiant energy vacuum drying of frozen pellets of CF extract is performed under one or multiple, e.g., 1, 2, 3, 4, or 5 drying conditions. A drying condition can be performed for about 2-11 hours using radiant energy of about 650 watts to about 1.3 kW (average power) under vacuum of less than about 100 mTorr, preferably 50-75 mTorr, at a maximum temperature of 35-38° C. Preferably, frozen pellets of CF extract are dried using two drying conditions comprising: (1) applying radiant energy of 1.026 kW under vacuum of about 50-75 mTorr for about 10.3 hours with a maximum temperature of 37.3° C. and (2) applying radiant energy of 1.165 kW under vacuum of about 50-75 mTorr for about 3 hours with a maximum temperature of 37.3° C.

The activity (e.g., yield of a specific protein in a cell free protein synthesis system) of the dried extract can be determined using assays such as performing cell free protein synthesis to produce a model protein (test protein) which can be measured. Methods for cell free protein synthesis are described in detail in, e.g., Kim, D.M. and Swartz, J.R. Biotechnol. Bioeng. 66:180-8 (1999); Kim, D.M. and Swartz, J.R. Biotechnol. Prog. 16:385-90 (2000); Kim, D.M. and Swartz, J.R. Biotechnol. Bioeng. 74:309-16 (2001); Swartz et al., Methods Mol. Biol. 267:169-82 (2004); Kim, D.M. and Swartz, J.R. Biotechnol. Bioeng. 85:122-29 (2004); Jewett, M.C. and Swartz, J.R., Biotechnol. Bioeng. 86:19-26 (2004); Yin, G. and Swartz, J.R., Biotechnol. Bioeng. 86:188-95 (2004); Jewett, M.C. and Swartz, J.R., Biotechnol. Bioeng. 87:465-72 (2004); Voloshin, A.M. and Swartz, J.R., Biotechnol. Bioeng. 91:516-21 (2005). Methods for measuring the production of a model protein in a cell-free transcription/translation reaction include the $^{14}C$ Leu incorporation assay, as described herein.

It has been discovered that additive containing bacterial extracts that have been freeze dried in the frozen state and afterwards stored at room temperature or 4° C. for greater than 175 days retained from at least 50% or more, e.g., 50%, 55%, 60%, 65%, 70% 75%, 80%, 85%, 90%, 95%, 99%, or 100% protein synthesis activity compared to additive-free, unfreeze dried extracts (control extracts). In some embodiments, the bacterial extract compositions described herein have greater than 70% (>70%, e.g., 70% 75%, 80%, 85%, 90%, 95%, 99%, or 100%)protein synthesis activity after storage of greater than 175 days, e.g., 176 days, 177 days, 178 days, 179 days, 180 days, 185 days, 190 days, 195 days, 200 days, 205 days, 210 days, 220 days, 230 days, 240 days, 250 days, 260 days, 270 days, 280 days, 290 days, 300 days, 310 days, 320 days, 330 days, 340 days, 350 days, 360 days, 365 days or more days at room temperature or 4° C.

Using the Karl Fischer coulometric titration method described below, it was determined that the additive-containing, freeze dried bacterial extracts have a water content of equal to or less than about 1.5%, e.g., 1.5%, 1.4%, 1.3%, 1.2%, 1.1%, 1.0%, 0.9%, 0.8%, 0.7%, 0.6%, 0.5%, 0.4%, 0.3%, 0.2%, 0.1% or 0%, (w/w) residual water. Some bacterial extracts have equal to or less than 1.0%, e.g., 1.0%, 0.9%, 0.8%, 0.7%, 0.6%, 0.5%, 0.4%, 0.3%, 0.2%, 0.1% or 0%, (w/w) residual water. Standard lyophilized extracts have a residual water content of at least 1% (w/w), e.g., 1%, 2%, 3%, 4%, 5% or more.

F. Methods for Measuring Water Content

Methods of measuring water content in a dried extract include proton nuclear magnetic resonance (NMR) spectrometry and Karl Fisher coulometric titration.

NMR spectrometry is based on the fact that a hydrogen proton has a magnetic moment and an angular momentum. Hydrogen atoms produce a magnetic field when they are excited by an alternating field from a transmitter in the presence of the Earth's static magnetic field. The relaxation field is produced by the protons excited by the excitation field. The amplitude of the relaxation field measured after the excitation is turned off is directly related to the number of protons that have been excited and, thus, to the water content. Time-domain nuclear magnetic resonance (TD-NMR) spectrometry and "Spin Track" NMR spectrometry are variations of this technique that have been applied to biological cultures and protein solutions.

For the purposes of the invention provided herein, the preferred method for measuring the percentage of water in a dried extract is Karl Fisher coulometric titration.

Karl Fischer titration utilizes the quantitative reaction of water with iodine and sulfur dioxide based on the Bunsen reaction in the presence of a primary alcohol such as methanol, ethanol or ethylene glycol monoethyl ether as the solvent, and an organic base such as pyridine as the buffering agent. Replacing the base with imidazole or primary amines may be utilized for a pyridine-free system. For protein or sugar solutions, a 2:1 methanol:formamide mixture may be used for solvent. Two variants in this method, the volumetric titration method and the coulometric titration method, utilize different iodine sources. In the volumetric titration method, the iodine required for reaction is previously dissolved and water content is determined by measuring the amount of iodine consumed as a result of reaction with water in a sample. Automatic volumetric titration systems are commercially available. In the coulometric titration method, iodine is first produced by electrolysis of a reagent containing iodide ion, then the water content is determined by measuring the quantity of electricity (Coulombs) [=electric current (Amperes)×time (seconds)] which is required for electrolysis in the production of iodine, based on the quantitative reaction of the generated iodine with water.

The Karl Fischer titration method can be performed using a drying oven (e.g., model D03080, Mettler Toledo, Columbus, Ohio) interfaced directly to a Karl Fisher coulometric titrator (e.g., model C20 from Mettler Toledo). Typically, the set point of the oven is set to 100° C. An aluminum insert is placed in the sample holder compartment of the oven and the extract to be measured is loaded into the insert through a port in the top of the oven. A nitrogen stream set at 200 mL/min is run through the oven to facilitate transfer of the water vapor from the oven to the titration vessel. The time between introduction of the sample to the oven and the start of the titration, or mix time, is set to 120 seconds to allow for complete transfer of the water in each sample to the titration vessel. The iodine for the titration is generated electrochemically in incremental amounts based on the drift observed by the instrument. The starting drift criterion is about less than about 25 μg/min. The drift criterion that should be achieved to end the measurement is less than about 3.0 μg/min, with a maximum titration time of about 3600 seconds. A voltametric sensor with a polarizing current of 5.0 µA (e.g., model DM143-SC) is used for detection. Each sample can be run in triplicate in order to capture variability in the measurements.

G. Using Freeze Dried Bacterial Extracts in Cell Free Protein Synthesis

Biologically active proteins of interest can be synthesized, properly folded and/or assembled using a cell-free protein synthesis system such as an Escherichia coli-based open cell-free (OCFS) system. In such a system, a cell extract from E. coli cells includes template DNA (such as plasmid or linear DNA fragments), amino acids (including native or non-native amino acids), nucleotides, T7 RNA polymerase, and an energy source. Optionally, disulfide isomerase chaperones is also added to aid in the formation of disulfide bonds. CFPS systems have been used to generate various proteins including growth factors (Zawada et al., Biotechnol Bioeng, 108:1570-1578 (2011)), full-length antibodies and antibody fragments (Yin et al., mAbs, 4(2):217-225 (2012)) and antibody-drug conjugates (Zimmerman et al., Bioconjug Chem, 25(2):351-61 (2014)).

The bacterial strain used to make the cell extract may have reduced nuclease and/or phosphatase activity which increases cell free synthesis efficiency. For example, the bacterial strain used to make the cell free extract can have mutations in the genes encoding the nucleases RNase E and RNase A. The strain may also have mutations to stabilize components of the cell synthesis reaction such as deletions in genes such as tnaA, speA, sdaA or gshA, which prevent degradation of the amino acids tryptophan, arginine, serine and cysteine, respectively, in a cell-free synthesis reaction. Additionally, the strain may have mutations to stabilize the protein products of cell-free synthesis such as knockouts in the proteases ompT or lonP.

In a generic CFPS reaction, a gene encoding a protein of interest is expressed in a transcription buffer, resulting in mRNA that is translated into the protein of interest in a CFPS extract and a translation buffer. The transcription buffer, cell-free extract and translation buffer can be added separately, or two or more of these solutions can be combined before their addition, or added contemporaneously.

To synthesize a protein of interest in vitro, the bacterial extract at some point comprises a mRNA molecule that encodes the protein of interest. In some systems, mRNA is added exogenously after being purified from natural sources or prepared synthetically in vitro from cloned DNA using RNA polymerases such as RNA polymerase II, SP6 RNA polymerase, T3 RNA polymerase, T7 RNA polymerase, RNA polymerase III and/or phage derived RNA polymerases. In other systems, the mRNA is produced in vitro from a template DNA; both transcription and translation occur in this type of reaction. In some embodiments, the transcription and translation systems are coupled or comprise complementary transcription and translation systems, which carry out the synthesis of both RNA and protein in the same reaction. In such in vitro transcription and translation systems, the bacterial extracts contain all the components (exogenous or endogenous) necessary both for transcription (to produce mRNA) and for translation (to synthesize protein) in a single system.

A CFPS reaction mixture can contain the following components: a template nucleic acid, such as DNA, that comprises a gene of interest operably linked to at least one promoter and, optionally, one or more other regulatory sequences (e.g., a cloning or expression vector containing the gene of interest) or a PCR fragment; an RNA polymerase that recognizes the promoter(s) to which the gene of interest is operably linked (e.g. T7 RNA polymerase) and, optionally, one or more transcription factors directed to an optional regulatory sequence to which the template nucleic acid is operably linked; ribonucleotide triphosphates (rNTPs); optionally, other transcription factors and co-factors therefor; ribosomes; transfer RNA (tRNA); other or optional translation factors (e.g., translation initiation, elongation and termination factors) and co-factors therefore; one or more energy sources, (e.g., ATP, GTP); optionally, one or more energy regenerating components (e.g., PEP/pyruvate kinase, AP/acetate kinase or creatine phosphate/creatine kinase); optionally factors that enhance yield and/or efficiency (e.g., nucleases, nuclease inhibitors, protein stabilizers, chaperones) and co-factors therefore; and; optionally, solubilizing agents. The reaction mix can also include amino acids and other materials specifically required for protein synthesis, including salts (e.g., potassium, magnesium, ammonium, and manganese salts of acetic acid, glutamic acid, or sulfuric acids), polymeric compounds (e.g., polyethylene glycol, dextran, diethyl aminoethyl dextran, quaternary aminoethyl and aminoethyl dextran, etc.), cyclic AMP, inhibitors of protein or nucleic acid degrading enzymes, inhibitors or regulators of protein synthesis, oxidation/reduction adjuster (e.g., DTT, ascorbic acid, glutathione, and/or their oxides), non-denaturing surfactants (e.g., Triton X-100), buffer components, spermine, spermidine, putrescine, etc. Components of such reactions are discussed in more detail in U.S. Pat. Nos. 7,338,789; 7,351,563; 8,715,958; and 8,778,631, the disclosures of each are incorporated by reference in their entirety for all purposes.

Depending on the specific enzymes present in the extract, for example, one or more of the many known nuclease, polymerase or phosphatase inhibitors can be selected and advantageously used to improve synthesis efficiency.

Protein and nucleic acid synthesis typically requires an energy source. Energy is required for initiation of transcription to produce mRNA (e.g., when a DNA template is used and for initiation of translation high energy phosphate for example in the form of GTP is used). Each subsequent step of one codon by the ribosome (three nucleotides; one amino acid) requires hydrolysis of an additional GTP to GDP. ATP is also typically required. For an amino acid to be polymerized during protein synthesis, it must first be activated. Significant quantities of energy from high energy phosphate bonds are thus required for protein and/or nucleic acid synthesis to proceed.

An energy source is a chemical substrate that can be enzymatically processed to provide energy to achieve desired chemical reactions. Energy sources that allow release of energy for synthesis by cleavage of high-energy phosphate bonds such as those found in nucleoside triphosphates, e.g., ATP, are commonly used. Any source convertible to high energy phosphate bonds is especially suitable. ATP, GTP, and other triphosphates can normally be considered as equivalent energy sources for supporting protein synthesis.

To provide energy for the synthesis reaction, the system can include added energy sources, such as glucose, pyruvate, phosphoenolpyruvate (PEP), carbamoyl phosphate, acetyl phosphate, creatine phosphate, phosphopyruvate, glyceraldehyde-3-phosphate, 3-Phosphoglycerate and glucose-6-phosphate, that can generate or regenerate high-energy triphosphate compounds such as ATP, GTP, other NTPs, etc.

When sufficient energy is not initially present in the synthesis system, an additional source of energy is preferably supplemented. Energy sources can also be added or supplemented during the in vitro synthesis reaction.

In some embodiments, the cell-free protein synthesis reaction is performed using the PANOx-SP system comprising NTPs, E.coli tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, phosphoenol pyruvate (PEP), NAD, CoA, $Na^{30}$ oxalate, putrescine, spermidine, and S30 extract.

In some embodiments, proteins containing a non-natural amino acid (nnAA) may be synthesized. In such embodiments, the reaction mix may comprise the non-natural amino acid, a tRNA orthogonal to the 20 naturally occurring amino acids, and a tRNA synthetase that can link the nnAA with the orthogonal tRNA. See, e.g., U.S. Pat. No. 8,715,958. Alternatively, the reaction mix may contain a nnAA conjugated to a tRNA for which the naturally occurring tRNA synthetase has been depleted. See, e.g., U.S. Pat. No. 8,778,631 and U.S. App. Publ. No. 2010/0184134. Various kinds of unnatural amino acids, including without limitation detectably labeled amino acids, can be added to cell free protein synthesis reactions and efficiently incorporated into proteins for specific purposes. See, for example, Albayrak, C. and Swartz, JR., Biochem. Biophys Res. Commun., 431(2):291-5; Yang WC et al., Biotechnol. Prog., (2012), 28(2):413-20; Kuechenreuther et al., PLoS One, (2012), 7(9):e45850; and Swartz JR., AIChE Journal, 58(1):5-13.

In some instances, the cell-free synthesis reaction does not require the addition of commonly secondary energy sources, yet uses co-activation of oxidative phosphorylation and protein synthesis. In some instances, CFPS is performed in a reaction such as the Cytomim (cytoplasm mimic) system. The Cytomim system is defined as a reaction condition performed in the absence of polyethylene glycol with optimized magnesium concentration. This system does not accumulate phosphate, which is known to inhibit protein synthesis. Detailed descriptions of the Cytomim system are found in, for example, U.S. Pat. No. 7,338,789; Jewett et al., Mol Syst Biol, (2008), 4:220; Spirin, A.S. and Swartz, J.R. (2008) Cell-free Protein Synthesis; Methods and Protocols, New Jersey:John Wiley & Sons, the contents are hereby incorporated in their entirety for all purposes.

The presence of an active oxidative phosphorylation pathway can be tested using inhibitors that specifically inhibit the steps in the pathway, such as electron transport chain inhibitors. Examples of inhibitors of the oxidative phosphorylation pathway include toxins such as cyanide, carbon monoxide, azide, carbonyl cyanide m-chlorophenyl hydrazone (CCCP), and 2,4-dinitrophenol, antibiotics such as oligomycin, pesticides such as rotenone, and competitive inhibitors of succinate dehydrogenase such as malonate and oxaloacetate.

In some embodiments, the cell-free protein synthesis reaction is performed using the Cytomim system comprising NTPs, E. coli tRNA, amino acids, $Mg^{2+}$ acetate, $Mg^{2+}$ glutamate, $K^+$ acetate, $K^+$ glutamate, folinic acid, Tris pH 8.2, DTT, pyruvate kinase, T7 RNA polymerase, disulfide isomerase, sodium pyruvate, NAD, CoA, $Na^+$ oxalate, putrescine, spermidine, and S30 extract. In some embodiments, the energy substrate for the Cytomim system is pyruvate, glutamic acid, and/or glucose. In some embodiments of the system, the nucleoside triphosphates (NTPs) are replaced with nucleoside monophosphates (NMPs).

The cell extract can be treated with iodoacetamide in order to inactivate enzymes that can reduce disulfide bonds and impair proper protein folding. As further described herein, the cell extract can also be treated with a prokaryotic disulfide bond isomerase, such as, not limited to, E. coli DsbC and PDI. The cell extract can be treated with DsbC, FkpA and peptidyl peolyl isomerase. Exogenous chaperone proteins can be expressed by the bacteria strain of the cell extract. Glutathione disulfide (GSSG) and glutathione (GSH) can also be added to the extract at a ratio that promotes proper protein folding and prevents the formation of aberrant protein disulfides.

In some embodiments, the CFS reaction includes inverted membrane vesicles to perform oxidative phosphorylation. These vesicles can be formed during the high pressure homogenization step of the preparation of cell extract process, as described herein, and remain in the extract used in the reaction mix.

The cell free synthesis reaction conditions may be performed as batch, continuous flow, or semi-continuous flow, as known in the art. The reaction conditions are linearly scalable, for example, the 0.3 L scale in a 0.5 L stirred tank reactor, to the 4 L scale in a 10 L fermentor, and to the 100 L scale in a 200 L fermentor.

The protein synthesis reactions described herein can utilize a large scale reactor, small scale, or may be multiplexed to perform a plurality of simultaneous syntheses. Continuous reactions can use a feed mechanism to introduce a flow of reagents, and may isolate the end-product as part of the process. Batch systems are also of interest, where additional reagents may be introduced to prolong the period of time for active synthesis. A reactor can be run in any mode such as batch, extended batch, semi-batch, semi-continuous, fed-batch and continuous, and which will be selected in accordance with the application purpose.

H. Methods for Comparing the Yield of Cell Free Protein Synthesis

The amount of protein produced in a CFPS reaction can be measured in any method known to one of skill in the art. One method relies on the availability of an assay which measures the activity of the particular protein being translated. An example of an assay for measuring protein activity is a luciferase assay system, or chloramphenicol acetyl transferase assay system for the production of the associated proteins. These assays measure the amount of functionally active protein produced from the translation reaction. Assays for measuring protein levels include, but are not limited to, coomassie-stained polyacrylamide gel, silver-stained polyacrylamide gel, ELISA, immunoblotting, Western blotting, size exclusion chromatography, affinity chromatography, and mass spectrometry. The activity of the particular protein being translated can be measured using any method known to one of skill in the art measures the activity (e.g., function) of the particular protein of interest. For example, the amount of particular kinase produced in a translation reaction can be measured by a kinase assay, wherein the activity of the particular kinase is determined by quantifying a kinase reaction.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Methods of measuring the capacity of an expression system to express a protein includes the $^{14}$C Leu incorporation assay. For the purposes of the invention provided herein, the preferred method for measuring the protein synthesis activity a dried extract is K he $^{14}$C Leu incorporation assay.

In a preferred assay, the yield of soluble protein is calculated from the amount of $^{14}$C Leu incorporated into soluble proteins produced in a cell free protein synthesis reaction. The extract can be treated with 50 μM iodoacetimide (IAM) for about 30 minutes at room temperature. IAM is added to allow for the formation of disulfide bonds within the protein of interest. Other thiol capping reagents such as iodoacetic acid (IAA) and N-ethyl maleimide (NEM) can be substitute for IAM.

Typically, the extract is then added to a microcentrifuge tube containing a protein synthesis reaction mixture with $^{14}$C Leu in order to initiate the reaction. About 60 μl of the reaction mix is transferred to a 24-well plate and spread evenly about the well. The mix is incubated at 30° C. for 5 hours. At the end of 5 hours the mix is transferred to a new microfuge tube. Two 10 μl aliquots are transferred to two slips of chromatography paper labeled "A" and "B". "A" represents total counts and "B" represents total protein counts. The remaining mix in the tube is centrifuged for about 15 minutes in a microfuge at about 13,000 rpm. Two 10 μl aliquots of the supernatant are transferred to two slips of chromatography paper labeled "C" and "D". "C" and "D" represent soluble protein. All slips of paper are dried at about 2 inches from a heat lamp for about 15 minutes. "A" is transferred to a microcentrifuge tube. "B", "C" and "D" are washed 3x with 5% TCA on ice for about 15 minutes, and then washed with 100% ethanol. They are then dried under a heat lamp for about 15 minutes. "B", "C" and "D" slip are transferred to individual microcentrifuge tubes. Scintillation cocktail (Optiphase Supermix, PerkinElmer, Waltham, MA) is added to each microcentrifuge and the slips are counted in a scintillation counter for 5 minutes.

The yield of total protein can be determined by the following equation:

(Counts slip B/counts slip A) (leucine concentration in cell free/# of leucines in protein of interest) (MW of protein of interest)

The yield of soluble protein of "C" and "D" can be determined by the following equation:

(Counts slip C or D/ counts slip A)(conc of leucine in CF/# leu residues in protein of interest)(MW of protein of interest)

The average yield of soluble protein can be determined by averaging the yield of "C" and "D".

Alternately, the yield of protein can be determined by running the protein labeled with $^{14}$C Leu on a polyacrylamide gel using conventional techniques. The gel can be denaturing or non-denaturing, according to the polypeptide to be detected. Where a protein containing multiple subunits is to be detected, a non-denaturing gel is preferred.

Alternatively, the yield of protein can be determined through specific binding assays such as enzyme linked immunosorbant assay (ELISA) or surface binding resonance (e.g., Biacore).

Alternatively, the yield of protein can be determined through whole or partial purification, such as using chromatography, coupled with protein quantitation, such as UV absorbance or BCA analysis.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

III. Examples

The following examples are provided by way of illustration only and not by way of limitation. Those of skill will readily recognize a variety of noncritical parameters that could be changed or modified to yield essentially similar results.

Example 1. Preparation of S30 E. coli Extracts

For preparation on a small scale, 10 μl of a thawed glycerol stock of E. coli was used to inoculate 50 ml of 2YT medium in a 250-mL baffled flask. The culture was incubated overnight at 37° C. with vigorous shaking. The 50 mL culture was then transferred into 1L of 2YTPG medium in a 2.5-L flask with a filter lining in the cap. The culture was incubated at 30° C. with vigorous shaking and monitored for growth rate. During the exponential phase and before the growth rate dropped during the transition to stationary phase, the cells were harvested and chilled. Once the culture was chilled, the cells were collected by centrifugation at 8,000 ×g for 20-30 minutes. Approximately 8 g of wet cells are collected from 1L at an OD of 3. The cell pellet was resuspended in at least 5 mL of S30 buffer for each gram of wet cell weight. The cell suspension was centrifuged at 8,000 ×g for 20-30 minutes. The supernatant was discarded and the washed cell pellet was frozen at −80° C.

For preparations on a large scale, the culture was harvested after 16-20 hours of fermentation. The fermenter (200 L fermenter) was then pressurized to 20 psi and the culture (~200L) is transferred, via pressure, to a chilled 200 L jacketed holding tank through two heat exchangers connected in parallel. The culture temperature in the holding tank (~200L) was cooled to 2-8° C. by re-circulating glycol through the jacket. Following the completion of the transfer, the culture was ready for the first centrifugation step via the disk stack centrifugation. During the first centrifugation step, the cells were separated from the spent medium (supernatant). The discharged paste (cell slurry) is collected into a container, weighed and then dispensed into a chilled 200L holding tank containing 100L of S30 buffer and mixed to re-suspend. The re-suspended cells were then centrifuged to pellet the cells. The cell pellet was stored at −80° C.

One liter of 2YTPG medium contains 16 g/L tryptone, 10 g/L yeast extract, 5 g/L sodium chloride, 22 mM sodium phosphate monobasic, 40 mM sodium phosphate dibasic, 100 mM glucose, and optionally 100 μl antifoam 204. 2YT medium contains 16 g/L tryptone, 10 g/L yeast extract, and 5 g/L sodium chloride. S30 buffer comprises 10 mM Tris acetate, 14 mM magnesium acetate and 60 mM potassium acetate.

Example 2. Processing of E. coli Cell Pellets into S30 Bacterial Extracts

Frozen S30 cell paste was broken into small pieces and thawed in 1 mL of room temperature S30 buffer per gram of cell paste. Once thawed, the cell suspension was kept on ice. The cell homogenizer was rinsed in S30 buffer prior to processing the cell extract. The cells were lysed by a single pass through the high pressure cell homogenizer at 17,500 psi. The lysate was then cooled quickly through a cooling coil or heat exchanger. The lysate was kept on ice until all the cell paste was lysed as described herein. The lysate was centrifuged at 30,000 ×g for 30 minutes at 4° C. The supernatant was collected into a clean tube and the centrifugation step was repeated once again in order to collect all supernatant in the lysate.

Pre-incubation mix contains 370 mM Tris acetate pH 8.2, 11.1 mM magnesium acetate, 16.5 mM ATP, 50 μM each of the 20 amino acids or non-native amino acids, 105 mM phosphoenol pyruvate (PEP), 8.4 U/mL pyruvate kinase.

Example 3. Formulating E. coli extracts with Additives

Liquid bacterial extract was formulated by mixing in concentrated stock solutions of additives to achieve various additive levels and combinations in the formulated extract. The additives used included mannitol, sorbitol, sucrose, trehalose, dextran, dextrin, glycerine, glycine, and raffinose. Over 150 formulation combinations were created and dried to evaluate extract formulations.

Example 4. Freeze Drying E. coli Extracts

This example illustrates three methods for using radiant energy vacuum one for conventional lyophilization method to dry cell-free extracts.

The first method (Liquid Extract Drying method) was used for drying a cell-free (CF) extract in a liquid state. About 0.5 ml of thawed CF extract was transferred into a sterile glass vial and capped. An aliquot of the thawed CF extract was reserved for further analysis as described below in Example 5. The vial was loaded into the radiant energy vacuum (REV) machine in which the caps are removed automatically. The sample in the REV machine was spun under vacuum at 500 rpm to reduce splashing under vacuum. When the temperature of the chamber reached 0-2° C., the microwave power was applied. The liquid drying conditions was as follows: a total drying time of 2,100 sec/0.5 ml; microwave power of 750 watts, spin speed of 200 rpm, and a maximum temperature of 35° C. The vial containing dried extract was capped, sealed with an aluminum cap, and stored at −80° C.

The second method (Frozen Extract Drying method) was used for drying a CF extract in a frozen state. About 1.0 ml of thawed CF extract was transferred into a sterile glass vial and capped. The vial was loaded into the radiant energy vacuum (REV) machine in which the caps are removed automatically. The sample in the REV machine was spun under vacuum at 500 rpm. When the temperature of the chamber reaches −20° C., the microwave power was applied. The freeze drying conditions include a total drying time of 3,000 sec/1.0 ml; microwave power of 750 watts, spin speed of about 200 rpm, and a maximum temperature of about 35-38° C. The vial containing dried extract was capped, sealed with an aluminum cap, and stored at −80° C.

The third method (Frozen Extract Pellet Drying method) was used for drying frozen pellets of CF extract. The CF extract was pelletized by releasing droplet of extract from a small gauge orifice positioned above a bath of liquid nitrogen. The resulting pellets were collect and stored at −80° C. Various size aliquots of the frozen pellets were loaded into an EnWave mpqRev lab unit for freeze drying. Typical radiant energy power was 800-3600 kW, under a vacuum of 30-200 mTorr, and drying lasting until the pellets reached above 15° C. as measured by an internal infrared temperature sensor. At the end of drying the dried extracts were transferred to a low humidity glovebox and aliquoted into tubes.

For comparison, frozen CF extract was lyophilized using a conventional method. Frozen CF extract was thawed in a 10° C. water bath kept in a 2-8° C. cold room. An aliquot of CF was placed in a glass vial and loaded into a standard lyophilizer such as VirTis Genesis Model EL. In the lyophilizer the extract is cooled to and maintained at −70° C. or lower, and vacuum pressure is applied to it until the frozen water in the extract sublimates.

The percentage of residual water in the dried extracts from all three microwave assisted drying methods and the conventional lyophilization were determined using the Karl Fisher (KF) coulometric titration method. In some instances the method was performed using a drying oven (e.g., model D03080, Mettler Toledo, Columbus, OH) interfaced directly to a Karl Fisher coulometric titrator (e.g., model C20 from Mettler Toledo). The set point of the oven was set to 100° C. An aluminum insert was placed in the sample holder compartment of the oven and the extract to be measured was loaded into the insert through a port in the top of the oven. A nitrogen stream set at 200 mL/min was run through the oven to facilitate transfer of the water vapor from the oven to the titration vessel. The time between introduction of the sample to the oven and the start of the titration, or mix time, was set to 120 seconds to allow for complete transfer of the water in each sample to the titration vessel. The iodine for the titration was generated electrochemically in incremental amounts based on the drift observed by the instrument. The starting drift criterion was about less than 25 μg/min. The drift criterion that must be achieved to end the measurement was less than 3.0 μg/min, with a maximum titration time of 3,600 seconds. A voltametric sensor with a polarizing current of 5.0 μA (e.g., model DM143-SC) was used for detection. Each sample was run in triplicate in order to capture variability in the measurements.

In other instances, KF measurement was performed by extracting water from 100-400 mg of pre-weighed dried extract using 1 ml of dry methanol, then centrifuging (14000 ×g for 1 min) the mixture and injecting 100 μl of the methanol supernatant into a Karl Fisher (KF) coulometric titrator (e.g., model AQUACOUNTER® AQ-300 from JM Science) to quantify the amount of water extracted.

Example 5. Measurement of Extract Activity in Cell Free Synthesis by $^{14}$C Leu Incorporation Assay The $^{14}$C Leu incorporation assay was one method used for quantitating protein (e.g., GM-CSF) produced from cell free synthesis reactions with cell free extracts.

Dried extracts were rehydrated by adding an appropriate amount of water to achieve the original unformulated extract volume, then lightly vortexed or inverted to mix. Frozen extracts were thawed in a room temperature bath just prior to assay. Each rehydrated or thawed extract was treated with 50 µM iodoacetimide for 30 minutes at room temperature. Then, the extract was added to a 96-well microplate containing a protein synthesis reaction mixture with $^{19}$C Leu in order to initiate the reaction. Each well contained 15 µl of reaction mix there were 3-12 replicate wells per extract sample. The mix was incubated at 30° C. for 8 hours. At the end of 8 hours the mix was quenched with 3x volumes of water. For each well, two 5 µl aliquots were transferred to two slips of chromatography paper labeled "A" and "B". Slip "A" represents total counts and slip "B" represents total protein counts. All slips of paper are dried on a hot plate for about 15 minutes. "A" was transferred to a microcentrifuge tube. Slip "B" was washed 3x with 10% TCA on ice for about 15 minutes, and then washed with 100% ethanol. They were then dried on a hot plate for about 15 minutes. Parafilm scintillant sheets were melted onto the slips, then cooled to solidify. The scintillant coated slips were counted in a scintillation counter for 5 minutes.

The yield of total protein was determined by the following equation:

(Counts slip B/counts slip A) (leucine concentration in cell free/# of leucines in protein of interest) (MW of protein of interest)

The average yield of total protein was determined by averaging the replicate wells for each sample.

Percent recovery of activity for dried extracts was calculated by the following equation:

(100%) (yield total protein from 400 µl of reaction mix using reconstituted dried extract)/(yield total protein from 400 µl of reaction mix using −80° C. frozen unformulated extract)

Example 6. Measurement of Extract Activity in Cell Free Synthesis by Protein Purification and Quantitation Protein purification and quantitation was a second method used for quantitating extract activity as measured by the extract's protein (e.g., IgG) production capability in a cell free synthesis reaction.

Dried extracts were rehydrated by adding an appropriate amount of water to achieve the original unformulated extract volume, then lightly vortexed or inverted to mix. Frozen extracts were thawed in a room temperature bath just prior to assay. Each rehydrated or thawed extract was treated with 50 µM-75 µM iodoacetimide for 30-60 minutes at room temperature. Then, the extract was added to a microplate containing a protein synthesis reaction mixture, at a ratio of maximize product yield, in order to initiate the reaction. Each well contained 1000 µl of reaction mix. The mix was incubated at 25° C.-35° C. for 14-18 hours. At the end of incubation the microplate is centrifuged and 400 µl of each supernatant transferred to a new microplate. Wells of the new plate were then contacted with chromatography resin (e.g., microbeads with Protein A ligand) contained within a pipet tip to adsorb the protein product. The beads were then washed and the product desorbed into 75 µl of elution buffer. UV absorbance is then used to determine the product concentration in the elution buffer, from which the product concentration in the cell free synthesis is calculated.

The average concentration of product protein was determined by averaging the replicate wells for each sample.

Percent recovery of activity for dried extracts was calculated by the following equation:

(100%) (yield total protein from 400 µl of reaction mix using reconstituted dried extract)/(yield total protein from 400 µl of reaction mix using −80° C. frozen unformulated extract)

Example 7. Performance of Freeze Dried E. coli Extracts Containing Formulation Additives This example illustrates that specific formulation additives for freeze drying extract can have a significant impact on the stability of dried extracts stored at moderate temperatures, as measured by degree of cell free activity recovery. For example, appropriately formulated dried cell-free extract (see Table 1 below) stored at room temperature maintained >70% recovered activity over 175 days, compared to unformulated cell-free extract which had <20% recovered activity when stored at room temperature for 19 days.

Aliquots of formulated and unformulated extracts were dried by the Frozen Extract Pellet Drying method (see Example 4), then stored in dry sealed tubes at various temperatures (e.g. −80° C., −20° C., 4° C., 20° C. and 37° C.) for various periods of time before being assayed for activity (activity assays described in Examples 3 and 4). Each time a dried extract was assayed, the corresponding −80° C. frozen unformulated extract was assayed as well and used as a reference for calculating percent activity recovery (described in Example 3 and 4).

The stability results for several formulations are shown in Table 1.

TABLE 1

| | | | | Stability as measured by percent activity recovery | |
|---|---|---|---|---|---|
| Formulation Sample # | w/v Ratio; total dry weight additives to volume unformulated extract (g/L) | Additive Composition (weight % of each additive in the additive mix) | Residual water (% w/w) | Stability at room temperature (20° C.-22° C.); percent recovery (number of days stored) | Stability at 4° C.; percent recovery (number of days stored) |
| No additives (unformulated) | 0 | N/A | 0.9% | 72% (7 days) 18% (19 days) | 82% (7 days) |
| #73 | 89 | 72% sorbitol 8% mannitol 20% dextran | 3.3% | 7% (124 days) | 85% (124 days) 68% (133 days) |
| #100 | 89 | 22% sucrose 22% sorbitol 46% mannitol 10% dextran | 3.7% | 62% (106 days) 31% (115 days) 44% (142 days) 46% (156 days) | 107% (106 days) 87% (115 days) 73% (142 days) 87% (156 days) |

TABLE 1-continued

Stability as measured by percent activity recovery

| Formulation Sample # | w/v Ratio; total dry weight additives to volume unformulated extract (g/L) | Additive Composition (weight % of each additive in the additive mix) | Residual water (% w/w) | Stability at room temperature (20° C.-22° C.); percent recovery (number of days stored) | Stability at 4° C.; percent recovery (number of days stored) |
|---|---|---|---|---|---|
| | | | | 35% (188 days) | 95% (188 days) |
| | | | | | 100% (784 days) |
| #150B | 89 | 22% sucrose | 0.5% | 90% (113 days) | 95% (113 days) |
| | | 22% sorbitol | | 83% (194 days) | 71% (194 days) |
| | | 46% mannitol | | 90% (440 days) | 95% (440 days) |
| | | 10% dextran | | 95% (742 days) | 107% (742 days) |
| #142 | 134 | 100% sucrose | 1.7% | 79% (26 days) | Not tested |
| | | | | 74% (53 days) | |
| | | | | 75% (178 days) | |
| #143 | 134 | 90% sucrose | 1.8% | 71% (26 days) | Not tested |
| | | 10% mannitol | | 74% (53 days) | |
| | | | | 80% (178 days) | |
| #144 | 89 | 100% sucrose | 1.1% | 88% (26 days) | 108% (178 days) |
| | | | | 80% (53 days) | 85% (505 days) |
| | | | | 84% (178 days) | |
| #145 | 45 | 100% sucrose | 2.6% | 115% (26 days) | Not tested |
| | | | | 100% (53 days) | |
| | | | | 85% (178 days) | |
| #146 | 45 | 90% sucrose | 2.2% | 106% (26 days) | Not tested |
| | | 10% mannitol | | 103% (53 days) | |
| | | | | 98% (178 days) | |
| #147 | 89 | 90% sucrose | 1.4% | 86% (26 days) | Not tested |
| | | 10% mannitol | | 97% (53 days) | |
| | | | | 95% (178 days) | |
| Trehalose | 70 | 100% trehalose | Not measured | 5% (1 day) | |
| #167 | 45 | 75% sucrose | 0.7% | 75% (211 days) | 81% (211 days) |
| | | 25% mannitol | | | 87% (500 days) |

Successful formulations were defined as those in which formulated dried extract showed >70% (greater than 70%) activity recovery after >175 days (greater than 175 days) storage at room temperature or 4° C. The formulations that met these criteria fell within the following formulation composition ranges:

The additive mix contained 90-100% (w/w) sucrose and 0-10% (w/w) mannitol, with an additive ratio range of 45-135 grams dry weight additives to liters of unformulated extract, and less than or equal to 1.5% (w/w) residual water in the dried extract.

The additive mix contained 20-25% (% w/w) sucrose, 20-25% (w/w) sorbitol, 45-50% (w/w) mannitol, 0-10% dextran; additive ratio range of 45-135 grams dry weight additives to liters of unformulated extract, and less than or equal to 1.5% (w/w) residual water in the dried extract.

The lyophilized bacterial extracts described in this example are protected against temperature and bacterial degradation. Such extracts have a longer self-life at room temperature and at 4-8° C. compared to control extracts, such as additive-free (unformulated) extracts. The results of the study show that the additive containing freeze dried bacterial extracts are useful in CFPS.

What is claimed is:

1. A freeze dried bacterial extract for cell free protein synthesis comprising:
   i. dried, lysed bacterial components, wherein the extract is able to synthesize upon rehydration a target protein from a template nucleic acid encoding the target protein; and
   ii. a carbohydrate composition in about 0.8-1.5:1.0 (w/w) ratio of carbohydrate to dried bacterial components, wherein the carbohydrate composition constitutes about 20-100% sucrose and a non-sucrose portion comprising mannitol, sorbitol, dextran or mixtures thereof.

2. The freeze dried bacterial extract of claim 1, wherein the carbohydrate composition constitutes 100% sucrose.

3. The freeze dried bacterial extract of claim 1, wherein the non-sucrose portion comprises at least about 75% of the carbohydrate composition.

4. The freeze dried bacterial extract of claim 1, wherein the extract has less than or equal to about 2.6% (w/w) residual water.

5. The freeze dried bacterial extract of claim 1, wherein the extract has less than or equal to about 1.5% (w/w) residual water.

6. The freeze dried bacterial extract of claim 1, wherein the extract when stored at about 20-22°C for 25 days or more and then is rehydrated has about 70% or more protein synthesis activity, compared to that of a control bacterial extract.

7. The freeze dried bacterial extract of claim 6, wherein the rehydrated extract has at least 80% protein synthesis activity.

8. The freeze dried bacterial extract of claim 7, wherein the extract prior to rehydrating is stored for 50 days or more.

9. The freeze dried bacterial extract of claim 7, wherein the extract prior to rehydrating is stored for 150 days or more.

10. The freeze dried bacterial extract of claim 6, wherein the extract prior to rehydrating is stored for 50 days or more.

11. The freeze dried bacterial extract of claim 6, wherein the extract prior to rehydrating is stored for 150 days or more.

12. The freeze dried bacterial extract of claim 6, wherein the control bacterial extract is stored at at least about −80° C.

13. The freeze dried bacterial extract of claim 1, wherein the bacterial extract has an active oxidative phosphorylation system in cell free protein synthesis.

14. The freeze dried bacterial extract of claim 1, wherein the bacterial extract is from an *Escherichia* species.

15. A freeze dried bacterial extract for cell free protein synthesis comprising:
   i. dried, lysed bacterial components, wherein the extract is able to synthesize upon rehydration a target protein from a template nucleic acid encoding the target protein; and
   ii. a carbohydrate composition in about 0.6-2.0:1.0 (w/w) ratio of carbohydrate to dried bacterial components, wherein the carbohydrate composition constitutes about 22% (% of total carbohydrate composition) sucrose, 22% sorbitol, 46% mannitol, and 10% dextran.

16. A freeze dried bacterial extract for cell free protein synthesis comprising:
   i. dried, lysed bacterial components, wherein the extract is able to synthesize upon rehydration a target protein from a template nucleic acid encoding the target protein; and
   ii. a carbohydrate composition in about 0.6-2.0:1.0 (w/w) ratio of carbohydrate to dried bacterial components, wherein the carbohydrate composition constitutes about 100% (% of total carbohydrate composition) sucrose.

17. A method of producing a target protein, the method comprising rehydrating the freeze dried bacterial extract of claim 1, wherein the freeze dried extract is able to synthesize the target protein from a template nucleic acid encoding the target protein in a cell free protein synthesis reaction, and synthesizing the target protein under conditions that support a cell free protein synthesis reaction by combining the rehydrated bacterial extract and a cell free protein synthesis reaction mixture.

18. The method of producing a target protein of claim 17, wherein the target protein comprises a non-natural amino acid.

19. The method of producing a target protein of claim 17, wherein the freeze dried extract comprises the template nucleic acid.

20. The method of producing a target protein of claim 17, wherein the cell free protein synthesis reaction mixture comprises the template nucleic acid.

21. A method of producing a target protein, the method comprising
   rehydrating the freeze dried bacterial extract of claim 15, wherein the freeze dried extract is able to synthesize the target protein from a template nucleic acid encoding the target protein in a cell free protein synthesis reaction, and
   synthesizing the target protein under conditions that support a cell free protein synthesis reaction by combining the rehydrated bacterial extract and a cell free protein synthesis reaction mixture.

22. The method of producing a target protein of claim 21, wherein the target protein comprises a non-natural amino acid.

23. The method of producing a target protein of claim 21, wherein the freeze dried extract comprises the template nucleic acid.

24. The method of producing a target protein of claim 21, wherein the cell-free protein synthesis reaction mixture comprises the template nucleic acid.

25. A method of producing a target protein, the method comprising
   rehydrating the freeze dried bacterial extract of claim 24, wherein the freeze dried extract is able to synthesize the target protein from a template nucleic acid encoding the target protein in a cell free protein synthesis reaction, and
   synthesizing the target protein under conditions that support a cell free protein synthesis reaction by combining the rehydrated bacterial extract and a cell free protein synthesis reaction mixture.

26. The method of producing a target protein of claim 25, wherein the target protein comprises a non-natural amino acid.

27. The method of producing a target protein of claim 25, wherein the freeze dried extract comprises the template nucleic acid.

28. The method of producing a target protein of claim 25, wherein the cell-free protein synthesis reaction mixture comprises the template nucleic acid.

* * * * *